(12) United States Patent
Ashenhurst

(10) Patent No.: US 7,909,845 B2
(45) Date of Patent: Mar. 22, 2011

(54) EPISTAXIS APPARATUS AND METHOD

(75) Inventor: Michael E. Ashenhurst, Calgary (CA)

(73) Assignee: Michael E. Ashenhurst, Calgary (CA)

( * ) Notice: Subject to any disclaimer, the term of this patent is extended or adjusted under 35 U.S.C. 154(b) by 894 days.

(21) Appl. No.: 11/601,935

(22) Filed: Nov. 20, 2006

(65) Prior Publication Data
US 2010/0016880 A1    Jan. 21, 2010

(51) Int. Cl.
*A61M 29/00*   (2006.01)
(52) U.S. Cl. ....................................................... 606/196
(58) Field of Classification Search ................. 606/196, 606/199, 108, 193, 202; 128/200.26, 201.18, 128/207.15, 202.13–202.19
See application file for complete search history.

(56) References Cited

U.S. PATENT DOCUMENTS

| 4,338,941 A * | 7/1982 | Payton | 606/196 |
| 7,108,706 B2 * | 9/2006 | Hogle | 606/199 |
| 2003/0105483 A1 * | 6/2003 | Hudson et al. | 606/196 |

* cited by examiner

*Primary Examiner* — Todd E Manahan
*Assistant Examiner* — Christopher Schubert
(74) *Attorney, Agent, or Firm* — Stephen M. De Klerk; SNR Denton US LLP

(57) ABSTRACT

An epistaxis apparatus for use with a sphygmomanometer having an arm cuff comprising: i) an air filled compressible rubber reservoir bulb sized to be received within the arm cuff for compression therein; ii) a flexible hose having one end connected to an end portion of the compressible bulb; and, iii) an inflatable nasal bladder having a front end portion connected to another end potion of the hose having an exterior shape generally sized to fill a nasal cavity. When the sphygmomanometer is pumped to a selected pressure, the nasal bladder expands within the nasal cavity to the selected pressure stopping a nose bleed. In a preferred aspect of this invention the nasal bladder comprises two similar side portions so that each nasal cavity of a user may receive one of the nasal bladders so that when the apparatus is pumped to the selected pressure each side portion will be similarly pressured and septal deviation with its associated discomfort will be avoided. Each side portion of the bladder further comprises a breathing tube extending through the bladder from a front to a rear side portion thereof so that after the side portions of the bladder are positioned and pressurized within the nasal cavity the user will be able to breath through the breathing tubes therein.

4 Claims, 1 Drawing Sheet

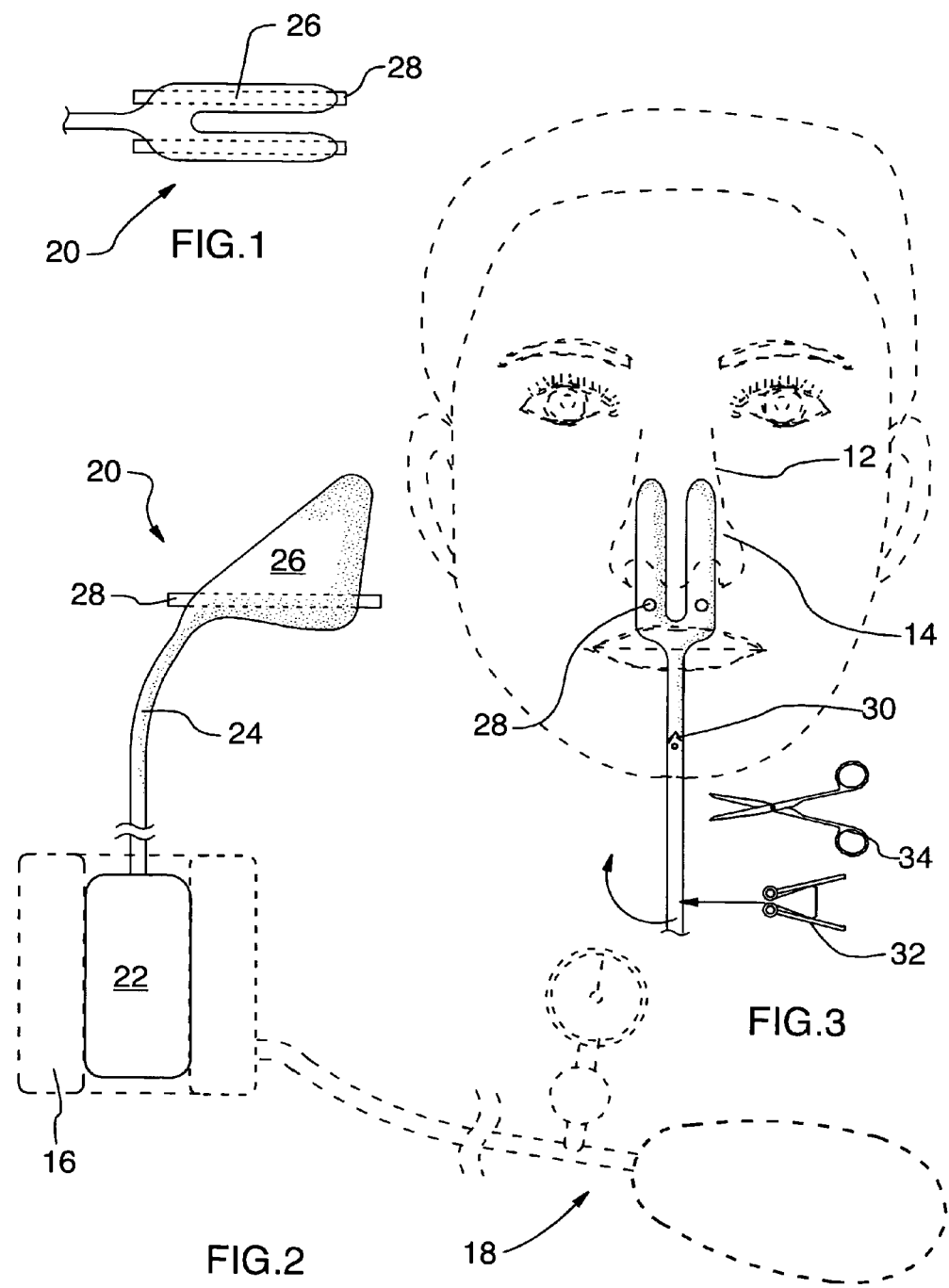

EPISTAXIS APPARATUS AND METHOD

FIELD OF THE INVENTION

This invention relates to apparatuses used to control epistaxis or nosebleeds. More particularly this invention relates to the use an epistaxis apparatus which is designed to be inflated to a specific pressure with a sphygmomanometer.

BACKGROUND OF THE INVENTION

Epistaxis is a frequent reason for emergency room visits. Epistaxis has been reported to occur in one of seven people in the United States. Epistaxis is more common in colder months and fry environments. The is a bimodal peak in the occurrence of epistaxis in those aged between 1-2 years and in those aged between 50-80 years. Mortality is rare but may occur due to hypovolemia and severe blood loss. Nasal packing is associated with increased morbidity. This includes sinusitis, septal haematoma or perforation, external nasal deformity, mucosal pressure necrosis, vasal-vagal episodes or balloon migration. Packing will usually cause airway compromise. Packing also may lead to infection. The most common strategies to achieve nasal packing are; VASELINE™ gauze packing, MEROCEL™ compressed sponges, and epistaxis balloons which may be either anterior (single) or anterior-posterior (double).

Some existing epistaxis packs are not pressurized. Those that are pressurized do not have a means to measure or to maintain pressure other than tactile feedback (i.e. feeling how tight the balloon is). Over inflation of epistaxis devices can cause necrosis of nasal tissues. Under inflation will render the devices ineffective. The pressure in the device may need to be maintained at various levels for extended periods of time. It will likely be useful to titrate the device pressure in relation to the patient's systolic and diastolic blood pressures. What is needed is a epistaxis device which allows for accurate pressurizing of the nasal cavity. The sphygmomanometer (blood-pressure) cuff is available in every medical treatment facility and at every hospital bedside. The sphygmomanometer cuff accurately reflects the pressure within the device very precisely in mm Hg. The sphygmomanometer allows for both accurate pressuring and precise pressure variation. Epistaxis devices are generally disposable. It is challenging to economically and cost-effectively provide a disposable epistaxis device which can accurately measure and regulate nasal pressure. What is needed is an epistaxis device which is easily attachable to a conventional sphygmomanometer so that the pressure pump, the pressure gauge, and the finely controlled air bleeding control of the sphygmomanometer can be used to accurately inflate and finely tune the air pressure within a disposable epistaxis device.

OBJECTS OF THE INVENTION

It is an object of this invention to disclose an epistaxis device which is easily attachable to a conventional sphygmomanometer so that the pressure pump, the pressure gauge, and the finely controlled air bleeding control of the sphygmomanometer can be used to accurately inflate and finely tune the air pressure within a disposable epistaxis device. It is an object of this invention to disclose an epistaxis apparatus which facilitates accurate pressure adjustment and as well as breathing, yet which is sufficiently inexpensive (due primarily to its reliance on relatively expensive sphygmomanometer components) that it can be supplied inexpensively on a disposable basis. It is yet a further object of this invention to disclose a method of using the disclosed epistaxis apparatus. It is final object of this invention to provide an effective epistaxis apparatus which is easy to insert an remove from the nose.

One aspect of this invention provides for an epistaxis apparatus for use with a sphygmomanometer having an arm cuff comprising: i) an air filled compressible rubber bulb sized to be received within the arm cuff for compression therein; ii) a flexible hose having one end connected to an end portion of the compressible bulb; and, iii) an inflatable nasal bladder having a front end portion connected to another end potion of the hose having an exterior shape generally sized to fill a nasal cavity. When the sphygmomanometer is pumped to a selected pressure, the nasal bladder expands within the nasal cavity to the selected pressure stopping a nose bleed.

In a preferred aspect of this invention the nasal bladder comprises two similar side portions so that each nasal cavity of a user may receive one of the nasal bladders so that when the apparatus is pumped to the selected pressure each side portion will be similarly pressured and septal deviation with its associated discomfort will be avoided. In the most preferred aspect of the invention each side portion of the bladder further comprises a breathing tube extending through the bladder from a front to a rear side portion thereof so that after the side portions of the bladder are positioned and pressurized within the nasal cavity the user will be able to breath through the breathing tubes therein.

Various other objects, advantages and features of this invention will become apparent to those skilled in the art from the following description in conjunction with the accompanying drawings.

FIGURES OF THE INVENTION

FIG. 1 is a partial front view of an epistaxis apparatus.
FIG. 2 is a side view of the epistaxis apparatus.
FIG. 3 is a partial front view of the epistaxis apparatus further comprising an optional one way valve.

The following is a discussion and description of the preferred specific embodiments of this invention, such being made with reference to the drawings, wherein the same reference numerals are used to indicate the same or similar parts and/or structure. It should be noted that such discussion and description is not meant to unduly limit the scope of the invention.

DESCRIPTION OF THE INVENTION

Turning now to the drawings and more particularly to FIG. 1 we have a partial front view of an epistaxis apparatus. FIG. 2 is a side view of the epistaxis apparatus. Most generally an epistaxis apparatus 20 for use with a sphygmomanometer 18 having an arm cuff 16 comprises: i) an air filled compressible rubber reservoir bulb sized 22 to be received within the arm cuff 16 for compression therein; ii) a flexible hose 24 having one end connected to an end portion of the compressible bulb 22; and, iii) an inflatable nasal bladder 26 having a front end portion connected to another end potion of the hose 24 having an exterior shape generally sized to fill a nasal cavity 14. When the sphygmomanometer 18 is pumped to a selected pressure, the nasal bladder 26 expands within the nasal cavity 14 to the selected pressure stopping a nose bleed. It should be noted that within this specification rubber is intended and defined to include any soft plastic or other similar synthetics which are resilient, flexible, and impervious to air.

In a preferred aspect of this invention the nasal bladder 26 further comprises two similar side portions so that each nasal cavity of a user may receive one of the nasal bladders 26. When the apparatus is pumped to the selected pressure each side portion will be similarly pressured and septal deviation with its associated discomfort will be avoided.

In the most preferred aspect of the invention the epistaxis apparatus 20 further comprises a breathing tube 28 extending through each side portion of the bladder 26 from a front to a rear side portion thereof so that after the side portions of the bladder 26 are positioned and pressurized within the nasal cavity 14 the user will be able to breath through the breathing tubes 28 therein. Most preferably the breathing tubes 28 are of sufficient diameter so that a user is able to breathe easily through a single tube if a naso-gastric tube is placed through an other of the two tubes 28.

In yet another aspect of the invention a one way valve 30 (see FIG. 3) is positioned in the hose 24 adjacent to the inflatable nasal bladder 26 so that the inflatable reservoir bulb 22 and substantially all of the hose 24 can be removed while the user is wearing the apparatus 20 simply by cutting the hose 24 adjacent to the one way valve on the bulb side of the hose 24 after the bladder 26 is inflated to the selected pressure. It is contemplated that the apparatus 20 will be manufactured in pediatric and adult sizes.

FIG. 3 is a partial front view of the epistaxis apparatus 20 further comprising an optional one way valve 30. Most generally, a method of using an epistaxis apparatus 20 comprising the following steps: a) directing the patient to blow his nose 12 to decrease the effects of local fibrinolysis and allow better visualization thereof; b) providing an appropriately sized apparatus 20 as described in claim 2 for the particular patient; c) unpackaging the apparatus wherein the nasal bladder portion 26 thereof is deflated; d) lubricating the nasal bladder portion thereof with an antibiotic ointment if the packaged apparatus is not prelubricated; e) fully inserting the deflated bladders 26 concurrently into both nares of the nose 12; and f) inflating the nasal bladder 26 by squeezing the reservoir bulb 22 to the desired pressure.

Most preferably in the above method, the reservoir bulb is not squeezed manually but with a cuff 16 of a sphygmomanometer 18 positioned over and around the reservoir bulb 22. The method further comprises the step of closing off the hose 24 adjacent to the nasal bladder 26 to maintain the selected pressure in the nasal bladder 26.

The above method may further comprise the step of folding over the hose 24 adjacent to the nasal bladder 26, then clamping 32, and finally cutting 34 the hose 24 beneath the clamp 32 after a stable internal pressure has been ascertained for more convenient ambience of the patient. When the apparatus 20 is provided is with a one way valve 30 the hose 24 then need not be folded but merely cut 34 beneath the one way valve 30 after a stable internal pressure has been ascertained for more convenient ambience of the patient.

While the invention has been described with preferred specific embodiments thereof, it will be understood that this description is intended to illustrate and not to limit the scope of the invention, which is defined by the following claims.

I claim:

1. A method of using an epistaxis apparatus comprising the following steps:
    a) directing the patient to blow his nose to decrease the effects of local fibrinolysis and allow better visualization thereof;
    b) providing an epistaxis apparatus appropriately sized for the particular patient for use with a sphygmomanometer having an arm cuff having:
        i) a compressible air filled rubber reservoir bulb sized to be received within the arm cuff for compression therein;
        ii) a flexible hose having one end connected to an end portion of the compressible bulb; and
        iii) an inflatable nasal bladder having a front end portion connected to another end portion of the hose having an exterior shape generally sized to fill a nasal cavity; so that when the sphygmomanometer is pumped to a selected pressure, the nasal bladder expands within the nasal cavity to the selected pressure first filling the infra-nasal cavity and then stopping a nose bleed, wherein the nasal bladder comprises two similar side portions so that each nasal cavity of a user may receive one of the nasal bladders so that when the apparatus is pumped to the selected pressure each side portion will be similarly pressured and septal deviation with its associated discomfort will be avoided;
    c) unpackaging the epistaxis apparatus wherein the nasal bladder portion thereof is deflated;
    d) lubricating the nasal bladder portion thereof with an antibiotic ointment if the packaged epistaxis apparatus is not prelubricated;
    e) fully inserting the deflated bladders concurrently into both nares of the nose;
    f) placing the arm cuff over and around the reservoir bulb; and
    g) inflating the nasal bladder to the selected pressure by squeezing the reservoir bulb with the sphygmomanometer.

2. A method as in claim 1 further comprising the step of closing off the hose adjacent to the nasal bladder to maintain the selected pressure in the nasal bladder.

3. A method as in claim 2 wherein the hose is closed off by folding over the hose adjacent to the nasal bladder, then clamping, and finally cutting the hose beneath the clamp after a stable internal pressure has been ascertained for more convenient ambience of the patient.

4. A method as in claim 1, further comprising the step of cutting the hose beneath a one way valve after a stable internal pressure has been ascertained for more convenient ambience of the patient.

* * * * *